(12) United States Patent
Dunleavy

(10) Patent No.: US 11,823,777 B2
(45) Date of Patent: Nov. 21, 2023

(54) SYSTEM AND METHOD FOR PROVIDING AN ON-DEMAND REAL-TIME PATIENT-SPECIFIC DATA ANALYSIS COMPUTING PLATFORM

(71) Applicant: Inovalon, Inc., Bowie, MD (US)

(72) Inventor: Keith R. Dunleavy, Annapolis, MD (US)

(73) Assignee: Inovalon, Inc., Bowie, MD (US)

( * ) Notice: Subject to any disclaimer, the term of this patent is extended or adjusted under 35 U.S.C. 154(b) by 265 days.

(21) Appl. No.: 17/236,679

(22) Filed: Apr. 21, 2021

(65) Prior Publication Data

US 2021/0287769 A1    Sep. 16, 2021

Related U.S. Application Data

(63) Continuation of application No. 15/087,821, filed on Mar. 31, 2016, now Pat. No. 11,011,256.

(60) Provisional application No. 62/269,924, filed on Dec. 18, 2015, provisional application No. 62/152,925, filed on Apr. 26, 2015.

(51) Int. Cl.
  *G16H 10/60* (2018.01)
  *G16H 50/20* (2018.01)

(52) U.S. Cl.
  CPC .............. *G16H 10/60* (2018.01); *G16H 50/20* (2018.01)

(58) Field of Classification Search
  CPC .............................. G16H 10/60; G16H 50/20
  USPC ........................................................ 705/2–3
  See application file for complete search history.

(56) References Cited

U.S. PATENT DOCUMENTS

| | | |
|---|---|---|
| 7,260,480 B1 | 8/2007 | Brown et al. |
| 7,590,550 B2 | 9/2009 | Schoenberg |
| 10,381,114 B2 | 8/2019 | Dunleavy |

(Continued)

FOREIGN PATENT DOCUMENTS

| | | |
|---|---|---|
| CN | 104765956 | 7/2015 |
| JP | 2003099541 | 4/2003 |

(Continued)

OTHER PUBLICATIONS

Anam et al., "A Summarization on Preserving Privacy Techniques in Data Mining," International Journal of Advanced Research in Computer Science, Nov.-Dec. 2014, 5(8):33-37.

(Continued)

*Primary Examiner* — Michael Tomaszewski
(74) *Attorney, Agent, or Firm* — Fish & Richardson P.C.

(57) ABSTRACT

A computing platform configured to receive and process an on-demand real-time patient-specific data analysis order is provided. The computing platform can receive an order, determine the viability of the order, and then perform the desired analysis based on parameters provided within the order. As part of the analysis, the computing platform can mine one or more data sources to collect data relevant to the ordered diagnostic. Once the data is collected, the computing platform can analyze the data according to one or more pre-programmed algorithms. The selection of which algorithms to apply to the data set can be determined by the type of on-demand real-time patient-specific data analysis ordered. The on-demand real-time patient-specific data analysis in some examples can be ordered using an external ordering user interface.

19 Claims, 10 Drawing Sheets

(56) References Cited

U.S. PATENT DOCUMENTS

| | | |
|---|---|---|
| 2001/0042050 A1 | 11/2001 | Fletcher et al. |
| 2002/0165735 A1 | 11/2002 | Stangel |
| 2003/0120515 A1 | 6/2003 | Geller |
| 2003/0149597 A1 | 8/2003 | Zaleski |
| 2004/0030224 A1* | 2/2004 | Sotos ............... A61B 5/4806 600/300 |
| 2004/0078222 A1 | 4/2004 | Khan et al. |
| 2004/0128163 A1 | 7/2004 | Goodman et al. |
| 2004/0158743 A1 | 8/2004 | Ham et al. |
| 2004/0176983 A1 | 9/2004 | Birkett et al. |
| 2005/0086360 A1 | 4/2005 | Mamou et al. |
| 2005/0149359 A1* | 7/2005 | Steinberg ............. G16H 50/20 705/2 |
| 2005/0197544 A1 | 9/2005 | Bernstein |
| 2005/0234740 A1 | 10/2005 | Krishnan et al. |
| 2005/0236474 A1 | 10/2005 | Onuma et al. |
| 2006/0047539 A1 | 3/2006 | Huang |
| 2006/0190295 A1* | 8/2006 | Merkin ................. G16H 50/70 705/2 |
| 2007/0011024 A1 | 1/2007 | Dale et al. |
| 2007/0016610 A1 | 1/2007 | Cohen et al. |
| 2008/0040151 A1 | 2/2008 | Moore |
| 2008/0046292 A1 | 2/2008 | Myers et al. |
| 2008/0228522 A1 | 9/2008 | Davis et al. |
| 2009/0080408 A1 | 3/2009 | Natoli et al. |
| 2009/0125333 A1 | 5/2009 | Heywood et al. |
| 2009/0217340 A1* | 8/2009 | Sitomer ................. G16H 10/60 726/1 |
| 2009/0254368 A1 | 10/2009 | Cunnold |
| 2010/0174557 A1 | 7/2010 | Bundschus et al. |
| 2010/0191071 A1* | 7/2010 | Anderson ............. G16H 50/50 703/11 |
| 2010/0223244 A1* | 9/2010 | Sinha ................. G06F 16/254 707/705 |
| 2011/0029325 A1 | 2/2011 | Georgiev et al. |
| 2011/0161105 A1 | 6/2011 | Hussam |
| 2011/0202486 A1* | 8/2011 | Fung .................. G16H 50/70 706/46 |
| 2011/0246229 A1 | 10/2011 | Pacha |
| 2012/0072460 A1 | 3/2012 | Friedlander et al. |
| 2012/0310661 A1 | 12/2012 | Greene |
| 2013/0191157 A1 | 7/2013 | Eiden et al. |
| 2013/0226601 A1* | 8/2013 | Razmi ................. G16H 10/20 705/2 |
| 2014/0006042 A1* | 1/2014 | Keefe ................. G16H 10/20 705/2 |
| 2014/0310025 A1 | 10/2014 | Sayada et al. |
| 2014/0357961 A1 | 12/2014 | Meltzer et al. |
| 2015/0066539 A1 | 3/2015 | Sheffer |
| 2015/0186604 A1 | 7/2015 | Chapman et al. |
| 2015/0227713 A1 | 8/2015 | Lynn et al. |
| 2015/0356094 A1 | 12/2015 | Gorelik |
| 2016/0012187 A1 | 1/2016 | Zasowski |
| 2016/0314249 A1 | 10/2016 | Dunleavy |
| 2018/0018432 A1 | 1/2018 | Dunleavy |

FOREIGN PATENT DOCUMENTS

| | | |
|---|---|---|
| JP | 2003108676 | 4/2003 |
| JP | 2004094621 | 3/2004 |
| JP | 2004258978 | 9/2004 |
| JP | 2004280807 | 10/2004 |
| JP | 2005515000 | 5/2005 |
| JP | 2007050254 | 3/2007 |
| JP | 2008527519 | 7/2008 |
| JP | 2011501276 | 1/2011 |
| JP | 2011501834 | 1/2011 |
| JP | 2013114270 | 6/2013 |
| JP | 2015170229 | 9/2015 |
| WO | WO 1998049632 | 11/1998 |
| WO | WO 2006072609 | 7/2006 |
| WO | WO 2009039230 | 3/2009 |
| WO | 2011257854 | 12/2011 |

OTHER PUBLICATIONS

Anonymous. (Dec. 4, 2015) "Health Level 7," Wikipedia, located at URL:https://en.wikipedia.org/w/index.php?title=Health_Level_7 &oldid=693713368 visited on Mar. 8, 2017, 5 pages.

Dunleavy, Office Action dated Feb. 1, 2016, directed to U.S. Appl. No. 14/886,876; 10 pages.

Google.com [online], "determining difference between a recommended treatment and actual," May 2017, [retrieved on May 14, 2017]. Retrieved from the Internet: URL https://www.google.com/search?q=determining+health+care+gaps+in+treatment+protocol, 2 pages.

Google.com [online], "determining health care gaps in treatment protocols," May 2017, [retrieved on May 14, 2017]. Retrieved from the Internet: URL https://www.google.com/search?q=determining+health+care+gaps+in+treatment+protocol, 2 pages.

Hage, "Intelligent Information Retrieval from Multiple Databases," Informatica e diritto, XIX annata, vol. II, 1993, n. 2, pp. 149-164 (Year: 1993).

International Preliminary Report on Patentability for WO/2017/106851 dated Jun. 19, 2018; 9 pages.

International Search Report and Written Opinion dated Mar. 16, 2017, directed to International Application No. PCT/US2016/067575; 8 paaes.

Japanese Patent Office; Notification of Reasons for Rejection mailed in counterpart Japanese patent application No. 2017-552501, with English-language translation (dated Jan. 8, 2019).

JP Office Action issued in Japanese Appln. No. 2019229251, dated Mar. 9, 2021, 11 pages (with English translation).

JP Search Report issued in Japanese Appln. No. 2019229251, dated Jul. 29, 2020, 32 pages (with English translation).

JP Office Action issued in Japanese Appln. No. 2019229251, dated Nov. 16, 2021, 4 pages (with English translation).

* cited by examiner

SYSTEM AND METHOD FOR PROVIDING AN ON-DEMAND REAL-TIME PATIENT-SPECIFIC DATA ANALYSIS COMPUTING PLATFORM

CROSS-REFERENCE TO RELATED APPLICATION

This application is a continuation of U.S. patent application Ser. No. 15/087,821, filed Mar. 31, 2016, which claims priority to U.S. Provisional Patent Application No. 62/152,925, filed Apr. 26, 2015, and U.S. Provisional Patent Application No. 62/269,924, filed Dec. 18, 2015, all of which are hereby incorporated herein by reference in their entirety.

FIELD OF THE DISCLOSURE

This disclosure relates generally to a computing platform that enables the on-demand analysis of various sets of available healthcare and healthcare-related data through interfaces within electronic order entry platforms and electronic health record systems, and the provision of the results of such analyses back through the same interfaces in real time.

BACKGROUND OF THE DISCLOSURE

Providing high-quality healthcare services while being vigilant of the costs associated with such healthcare has traditionally been a goal of healthcare providers and related businesses. In a healthcare environment in which patients visit multiple doctors and healthcare providers across large geographic areas that may or may not communicate with one another, performing medical diagnostics or other tests to ascertain pertinent information about a patient can be inefficient due to the fact that tests and medical diagnoses may be duplicated amongst various healthcare providers that a patient has visited or may be performed without the benefit of information known and available from other healthcare providers.

Furthermore, the healthcare landscape is growing increasingly complex, which also can create tension with the goal of high-quality healthcare at low cost. The number of disease conditions known to clinicians is ever increasing as scientific discovery details a more granular understanding of pathogenesis, genetics, and sub-segmentation of previously less-understood conditions. The coding granularity by which such conditions are reflected within medical record documentation is similarly rising, as exemplified by the transition from ICD-9 (containing approximately 14,000 diagnosis codes) to ICD-10 (containing approximately 68,000 diagnosis codes) standards. The number and type of diagnostics available to clinicians is ever increasing, as is the number of treatment modalities.

In addition to the aforementioned rise in detailed granularity and complexity within the core practice of medicine, the business process, administration, and regulatory oversight surrounding healthcare is similarly rising in its complexity. Quality outcomes measurement metrics have risen dramatically in importance as the healthcare industry transitions froth volume-based to value-based care. The ability to assess the quality of care a patient has received in the past can be paramount to driving optimized healthcare decisions as well as driving healthcare costs down. However, often times the data required to make such an assessment can be stored in disparate places and entities that do not communicate with one another. Furthermore, the information required to make such assessments can be voluminous, thus making it untenable for a healthcare provider to make a "real-time" (during the period of a clinical encounter) assessment about the quality of care a patient has received and whether or not their care has complied with regulatory standards.

Computing platforms, in which data is aggregated, mined, and analyzed from multiple sources to put together a comprehensive and in-depth view of various facets of a patient's medical history "on-demand" (when needed and requested), can help to maximize the quality of healthcare while at the same-time minimizing inefficient expenditures associated with performing unnecessary or redundant medical tests and laboratory diagnostics. However, the aforementioned aggregation, mining, and analysis is often based upon large amounts of data that are spread over many different sources, and thus it is untenable for a healthcare provider to perform such analytics.

SUMMARY OF THE DISCLOSURE

This disclosure relates to a computerized platform for performing analytics using medical data aggregated and mined from various third-party and internal databases. The platform can allow for the real-time analysis of a patient's medical data and allows for a healthcare provider to order an analytical test that is most pertinent to the patient and healthcare provider, on demand, at the time of the medical encounter, and receive the answer back to support the clinician's provision of high quality and cost-effective care.

DETAILED DESCRIPTION

Figure 1:
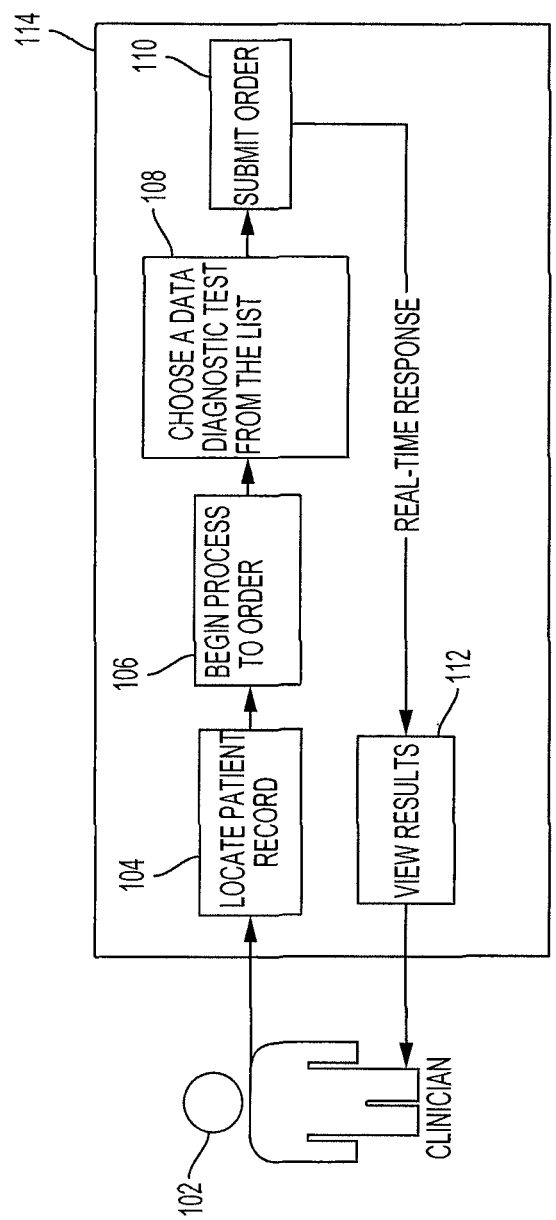
FIG. 1 illustrates an exemplary method for performing an on-demand real-time patient-specific data analysis (sometimes referred to as a "Data Diagnostic" or "Data Diagnostics") according to examples of the disclosure.

An on-demand real-time patient-specific data analysis, in one example, can be a suite of numerous patient-specific data analyses that can be ordered individually by clinicians at the point of care. Ordering a real-time patient-specific data analysis can, in some examples, initiate a process that includes mining multiple databases to retrieve information related to a specific patient, collecting the information related to that patient, and analyzing the collected information for specific features or patterns that can assist a doctor or healthcare provider to provide a higher-quality and more cost-effective patient experience.

An example scenario can help to illustrate the concept of performing a real-time patient-specific data analysis. In the example scenario a patient is brought into an emergency room unable to provide information due to their state of acute distress, trauma, or state of unconsciousness. Typically, because the patient is unable to reliably answer questions relating to their medical history, a clinician providing care would have to perform a vast series of medical tests to not only diagnose the medical issue but also to ensure that there are no other complicating factors that could affect a course of treatment prescribed by the clinician. Further, the physician may be unable to determine whether an abnormal finding is acute or chronic, or whether previous treatments had adverse impacts such as allergic reactions, thus complicating the determination of active issues and associated appropriate care. However, if a clinician was able to order an on-demand real-time patient-specific data analysis for a patient, a computing platform could mine multiple data sources (i.e., other clinicians' databases, historical diagnosis data, pharmaceutical records, laboratory records, electronic medical record data, etc.), collect information relating to the patient's past medical history and care, perform an analysis on the collected information, and determine factors or other pertinent information that may aid the healthcare provider in providing treatment to the patient that is unable to be adequately or reliably responsive, poorly responsive, or unconscious in the emergency room. In one example, an on-demand real-time patient-specific data analysis could retrieve information relating to medications a patient has taken or is currently taking, all previous lab work that was performed on the patient, prior diagnoses, and prior admissions to hospitals. The information retrieved by the on-demand real-time patient-specific data analysis can be all located within a single database or, in some examples, can be located in various disparate databases maintained by third-party healthcare providers. The computing platform can mine each of these databases to see if there is pertinent information stored in a particular database that relates to the patient for which an on-demand real-time patient-specific data analysis is ordered.

In substantially the same manner that a clinician can order laboratory tests to determine the best course of treatment for a patient, a clinician could also order a real-time patient-specific data analysis to initiate a process in which data relating to a specific patient could be mined and analyzed to inform the course of care.

FIG. 1 illustrates an exemplary method for performing an on-demand real-time patient-specific data analysis according to examples of the disclosure. As illustrated in FIG. 1, a clinician 102 can initiate an on-demand real-time patient-specific data analysis process using a laboratory diagnostic order entry interface or other order entry interface 114. Order entry interface 114 can, in some examples, be a preexisting computer interface utilized by, for example, a laboratory service provider to order laboratory tests or by a clinician to order a prescription drug directly from a particular pharmacy. By utilizing a preexisting order entry interface, a healthcare provider can have a common interface to order both laboratory diagnostics as well as on-demand real-time patient-specific data analyses for a particular patient under their care within their existing workflow. In some examples, the on-demand real-time patient-specific data analysis can be ordered using a separate interface dedicated to interfacing with an on-demand real-time patient-specific data analyses computing platform (discussed in detail below).

Once a clinician 102 initiates an on-demand real-time patient-specific data analysis, the process can move to step 104 wherein a patient record is located. At step 104, the order entry system can attempt to search for a patient's records which can include their name, date of birth, age, and other identifying information that can ensure that any test ordered (i.e., an on-demand real-time patient-specific data analysis or a lab diagnostic) pertains to the person that the clinician or healthcare provider intended.

Once the patient has been identified at step 104, the process can move to step 106, in which the process to order a test can be initiated. In the example of an on-demand real-time patient-specific data analysis, at step 108 the healthcare provider can be prompted to choose an on-demand real-time patient-specific data analysis test from a list of available tests.

Types of On-Demand Real-Time Patient-Specific Data Analyses

The following discussion of types of on demand real-time patient-specific data analyses is meant for exemplary purposes and should not be construed as an exhaustive list or a limiting of the scope of the on-demand real-time patient-specific data analyses computing platform.

In one example, a clinician may want to ascertain the quality of care a patient has received. Furthermore, the healthcare provider may want to assess the quality based on a national standards of care such as NCQA/HEDIS®, Medicare Advantage 5-star rating measures, URAC measures, state-specific standards (e.g., NY QARR measures), commercial ACA QRS measures, PQRI measures, or any other applicable measures so that clinicians can assess a patient's quality of care and know where a patient stands and how to improve their quality of care. In such an example, a healthcare provider could order a quality-related on-demand real-time patient-specific data analysis in which data relating to a patient's past medical history is mined and analyzed to assess the quality of care that a patient has received and what remedial steps are to be undertaken to bring the patient within an applicable standard of care.

In another example, a clinician, hampered by a lack of insight into the comprehensive medical history of a new patient, a complex patient, or a patient who cannot provide details about their medical past, may need or want more information regarding their patient's medical history. In such a scenario, a medical practitioner may wish to order a historical data-related on-demand real-time patient-specific data analysis in which electronic health records of various medical entities are mined for information relating to a patient's past clinical diagnoses, prescribed medications, laboratory results, surgical procedures, etc.

In another example, a physician may want to ascertain a patient's historical medical condition(s) and their progression, but often has limited insight into all of the patient's diseases and comorbidities and limited expertise in risk score-coding accuracy requirements. In such a scenario, a healthcare provider can order a risk score-related data diagnostic in which data is mined and analyzed to determine historical, current, and predictive disease burdens and risk scores of a specific patient within a relevant risk score model.

In another example, a healthcare provider may struggle to avoid duplication of tests and often lack insight into how often, how recently, or what the results may be from similar tests that have been performed, or the parameters mandated by the organization responsible for patient costs for care consideration, such as formulary adherence, appropriate diagnostic imaging guidelines, and specialist care. In such a scenario, a healthcare provider could order a waste-avoidance related on-demand real-time patient-specific data analysis. A waste-avoidance related on-demand real-time patient-specific data analysis can mine and analyze data relating to a patient to search for information pertinent to identifying potentially unnecessary utilization and cost related to benefits coverage guidelines for patient care, and even find less costly alternatives.

In another example of the types on-demand real-time patient-specific data analyses, a physician may want to determine various care-management resources for which a patient may be eligible. However, such a task may be difficult because often a clinician is unable to know of any federal, state, and healthcare organization-specific programs that a patient may be eligible for. In such a scenario, a clinician can order an eligibility-related on demand real-time patient-specific data analysis that aggregates, mines and analyzes data related to the programs and a patient's eligibility for those programs.

Returning to the example of FIG. 1, once a clinician has selected the type of on-demand real-time patient-specific data analysis that they wish to order for their patient, the process can move to step 110, in which an order for the diagnostic is submitted to an external computing platform that will aggregate and mine various data sources for information relating to the ordered data diagnostic, perform an analysis on the aggregated and mined data, and construct a resulting report to deliver a result to the healthcare provider. At step 112, the healthcare provider can view the results provided by the computing platform, having received the analysis is real time.

Figure 2:
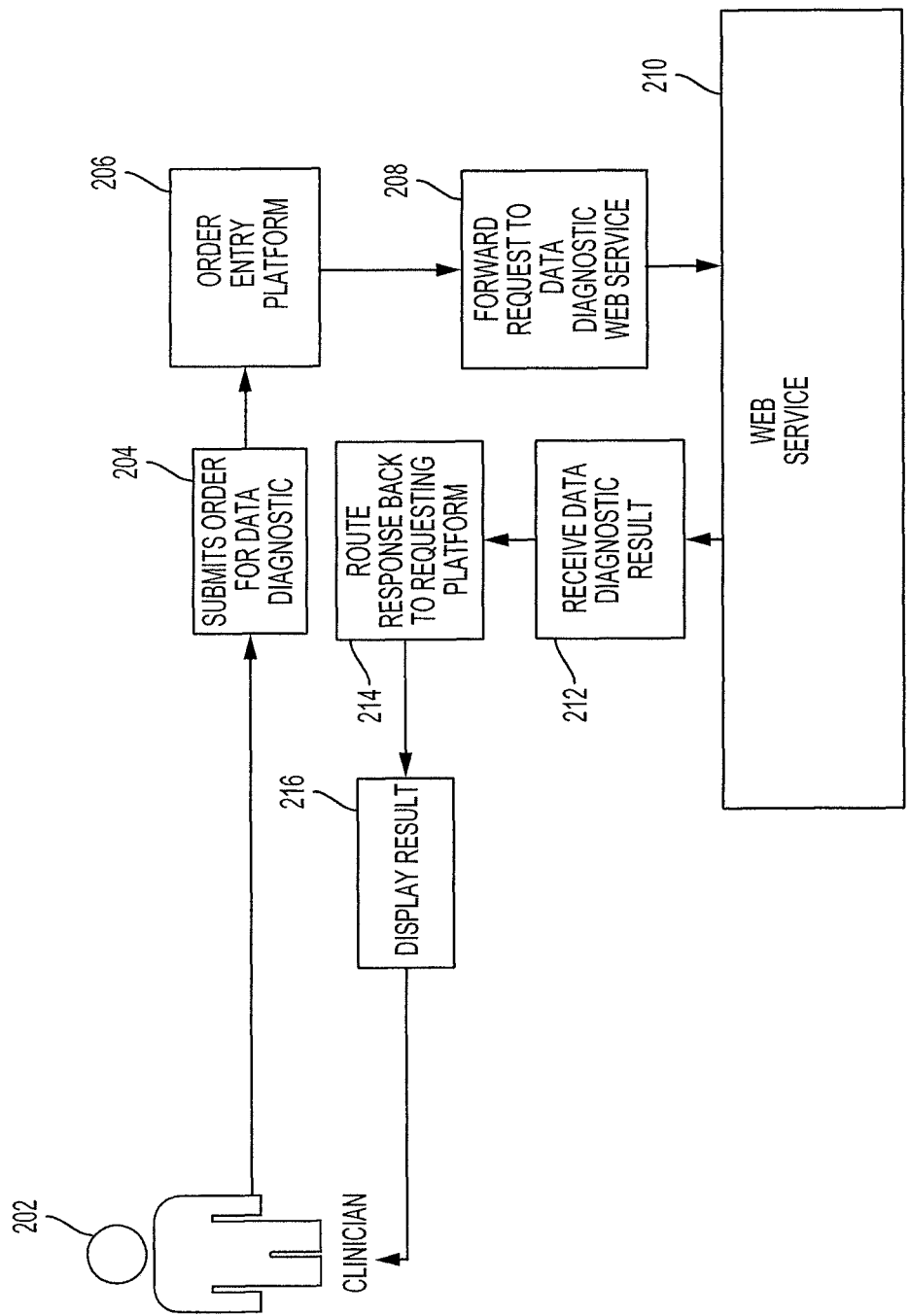
FIG. 2 illustrates another exemplary method for performing an on-demand real-time patient-specific data analysis according to examples of the disclosure.

The process from when the order is submitted at step 110 and when the results are viewed at step 112 can include submitting the order to a computing platform that is to perform the requested analysis. FIG. 2 illustrates another exemplary method for performing an on-demand real-time patient-specific data analysis according to examples of the disclosure. Similar to the method described in FIG. 1, a clinician 202 can submit an order for an on-demand real-time patient-specific data analysis at step 204. At step 206, the order can be received by a lab information system or other order entry platform. The information system or order entry platform can view the submitted order and determine if the order is for a traditional lab diagnostic, prescription drug, or other traditional order, or whether the order is for an on-demand real-time patient-specific data analysis. If it is determined that the order is for an on-demand real-time patient-specific data analysis, the process can move to step 208 wherein the order is forwarded to an on-demand real-time patient-specific data analysis service provider (discussed in detail below). At step 210, the on-demand real-time patient-specific data analysis service provider can utilize a web service to parse the request, aggregate, mine and analyze the desired data, and generate a result/report of the on-demand real-time patient-specific data analysis. At step 212 the result can be received and routed back to the requesting service provider.

Figure 3:
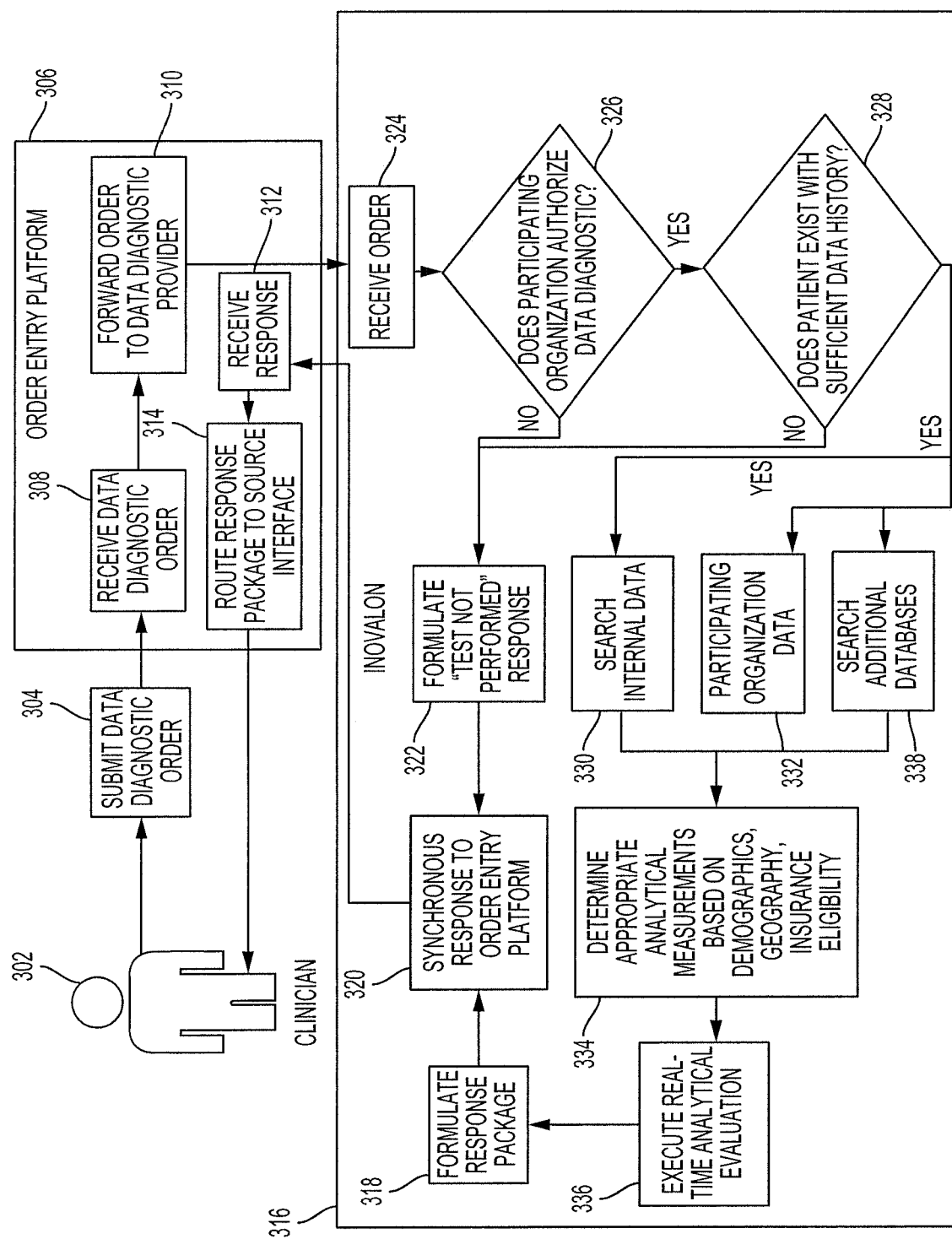
FIG. 3 illustrates another exemplary method for performing an on-demand real-time patient-specific data analysis according to examples of the disclosure.

FIG. 3 illustrates an exemplary functionality of an on-demand real-time patient-specific data analysis web service according to examples of the disclosure. Clinician 302 can submit an on-demand real-time patient-specific data analysis order at step 304, as described above with respect to FIGS. 1 and 2. The on-demand real-time patient-specific data analysis order can be received by an order entry platform 306. As previously discussed, an on-demand real-time patient-specific data analysis can be ordered by employing the same computing platform that is used by a laboratory services provider, pharmacy, or other electronic or order entry platform. As an example, a healthcare provider that utilizes a commercial laboratory services provider can employ the electronic user interface used to order laboratory services to also order on-demand real-time patient-specific data analyses. As another example, a healthcare provider that utilizes an electronic medical record system which supports order entries can employ the electronic user interface used to also order data diagnostics.

As part of the process of ordering the on-demand real-time patient-specific data analysis, a healthcare provider can include inclusion criteria as part of the order. Inclusion criteria can include types of analyses or sets of data that the practitioner wishes to be included in the real-time patient-specific data analysis. As an example, if a doctor wishes to order a quality-related on-demand real-time patient-specific data analysis, the practitioner may want to include certain standards of care, such as Medicare Advantage 5-star rating measures, from the analysis for various reasons. The practitioner, in that instance, can employ the user interface to specify that the Medicare standard should be included in the on-demand real-time patient-specific data analysis.

Additionally, as part of the process of ordering the on-demand real-time patient-specific data analysis, a healthcare provider can include exclusion criteria as part of the order. Exclusion criteria can include types of analyses or sets of data that the practitioner wishes to be excluded from the on-demand real-time patient-specific data analysis. The healthcare provider can order a general analysis of all available quality measures, or the provider can provide exclusion criteria that chooses specific programs (such as NCQA or HEDIS), which includes a subset of measures, or the provider can select individual measures.

When ordering a specific on-demand real-time patient-specific data analysis, the practitioner can also be presented a hierarchical menu of choices, with each tier of the hierarchy being dependent on the selections made by the practitioners on the tier before it. In one example, if the practitioner decides that they only want to perform a Medicaid analysis, they can then specify the type of program (i.e., adult program, child program) and can also specify the state, such as New York, Florida, California, etc. In this way, the hierarchical menu can generate a set of inclusion and exclusion criteria that is transmitted to the on-demand real-time patient-specific data analysis web service and is used by the web service to perform the desired analysis.

In some examples, the inclusion and exclusion criteria can be generated by the computing platform/web service. For example, a clinician can order a quality-related diagnostic. Based on the information relating to the specific patient, the computing platform can generate inclusion and exclusion criteria. For instance, if the computing platform recognizes that a particular patient is a Medicare patient in the state of New York, and is also a Medicaid patient, the platform can identify the quality standards that are to be evaluated for the apparently dual eligible patient, rather than having the clinician make those determinations. In another example, a clinician may be unaware of the different clinical quality standards applicable to a patient. In such cases, wherein the clinician therefor orders a high level hierarchical on-demand real-time patient specific data analysis, the computing platform recognizes the applicability of the relevant quality standards for the respective patient, and applies the applicable analysis.

In other examples, the on-demand real-time patient-specific data analysis can be ordered using a stand-alone user interface that is linked directly to an on-demand real-time patient-specific data analysis computing platform/web service. In the example of FIG. 3, in which a laboratory services provider's user interface is employed, order entry platform 306 can receive the on-demand real-time patient-specific data analysis order at step 308. At step 310, the on-demand real-time patient-specific data analysis order can be forwarded to an on-demand real-time patient-specific data analysis computing platform/web service for processing.

The on-demand real-time patient-specific data analysis computing platform 316 can receive the order at step 324. The order generated by the healthcare provider can include information about the patient receiving care, including their name and other identifying information (such as date of birth, social security number, insurance information, etc.) so as to ensure that the computing platform is performing the analysis on the patient for which the healthcare provider has ordered the on-demand real-time patient-specific data analysis. At step 326, a preliminary check can be conducted to ensure that the patient's insurance carrier or other relevant organization such as an accountable care organization, hospital, or shared risk entity, authorizes and will cover the costs of the on-demand real-time patient-specific data analysis that has been ordered by the healthcare provider. If it is determined that the insurance carrier or other relevant organization does not authorize the on-demand real-time patient-specific data analysis, the process can move to step 322, wherein a "test not performed" message can be generated. At step 320 the "test not performed" message can be synchronized to the ordering system order message format (discussed in detail below) and can be sent to the ordering system at step 312. Finally, at step 314 the response can be routed back to the healthcare provider, indicating that the on-demand real-time patient-specific data analysis was not performed due to insurance carrier or other relevant organization not authorizing it.

If, however, the insurance carrier or other relevant organization authorizes the on-demand real-time patient-specific data analysis, the process can move to step 328, wherein the computing platform can ascertain whether the patient exists within the on-demand real-time patient-specific data analysis web service system and if there is sufficient data history to conduct an analysis. Such an analysis can be performed by a qualifying algorithm. A qualifying algorithm can determine whether the system is adequately confident in establishing the identity of the patient and is adequately confident that there is enough data to perform an analysis.

If the qualifying algorithm establishes that there is adequate confidence that the patient exists within the system and that there is sufficient data history to perform the on-demand real-time patient-specific data analysis, the process can move to steps 330 332, and 338. At step 330 an internal database (or other data storage entity) can be mined to extract information that is relevant to the ordered on-demand real-time patient-specific data analysis.

The internal database can be a database that is stored locally within the computing platform. The database can be constituted by de-identified and longitudinally matched information provided to it by various participating organizations. As an example, if an insurance carrier such as Blue Cross Blue Shield (BCBS) participates in providing its patients with on-demand real-time patient-specific data analyses service, then BCBS can provide the computing platform with all of the data it has on its patients. That data can be internalized and stored within a database that is maintained by the computing platform itself. Such datasets can be established and maintained through batch or transactional data provision processes.

Thus, when a physician orders an on-demand real-time patient-specific data analysis, the order is interpreted as on behalf of and for the benefit of the patient's treatment, and thus the internal database can be mined and analyzed to identify and extract information relating to a particular patient. In doing so, the de-identified data stored within the internal database can be extracted and re-identified as belonging to the patient for which the on-demand real-time patient-specific data analysis was ordered.

The internal database can contain multiple data sets, each data set corresponding to data provided by a particular participating organization. In one example, one data set can belong to BCBS patients while another data set can belong to a laboratory services provider. Thus, when a patient's clinician requests an on-demand real-time patient-specific data analysis, depending on the identity of the patient as well as other inclusion and exclusion criteria, the computing platform can extract data from the relevant data sets stored in the internal database, re-identify, and, if necessary, longitudinally match that data based on the identity of the patient, and combine it together in one location to be analyzed. Once the data has been analyzed, the combined data can be deleted (with the original data sets remaining intact) so that the data is de-identified.

At steps 332 and 338 the computing platform can also mine data from various external databases provided by third parties. As an example, rather than have healthcare providers or healthcare entities provide their data to the computing platform to be stored in the internal database, the data can be maintained and stored at a third-party database. The computing platform can access those databases and mine them for data relevant to the patient asking for the on-demand real-time patient-specific data analysis as well as the on-demand real-time patient-specific data analysis itself.

Once the data has been mined from the various databases, at step 334 the computing platform can determine the appropriate analytical processes to be employed to produce the results desired by the clinician 302. The creation of algorithms that not only determine which analytical measurements to employ but how those analyses are implemented is discussed in further detail below. At step 336, the computing platform 316 can execute the real-time analysis of the data mined from the various data sources using the analytical measurements determined in step 334.

Once the analysis has been performed at step 336, a response package can be created at step 318. The formulation of the response package is described in further detail below. At step 320, the response package can be transmitted back to the order entry platform 306 at step 320. The order entry platform 306 can receive the response at step 312 and route the response package back to the healthcare provider at step 314.

Figure 4:
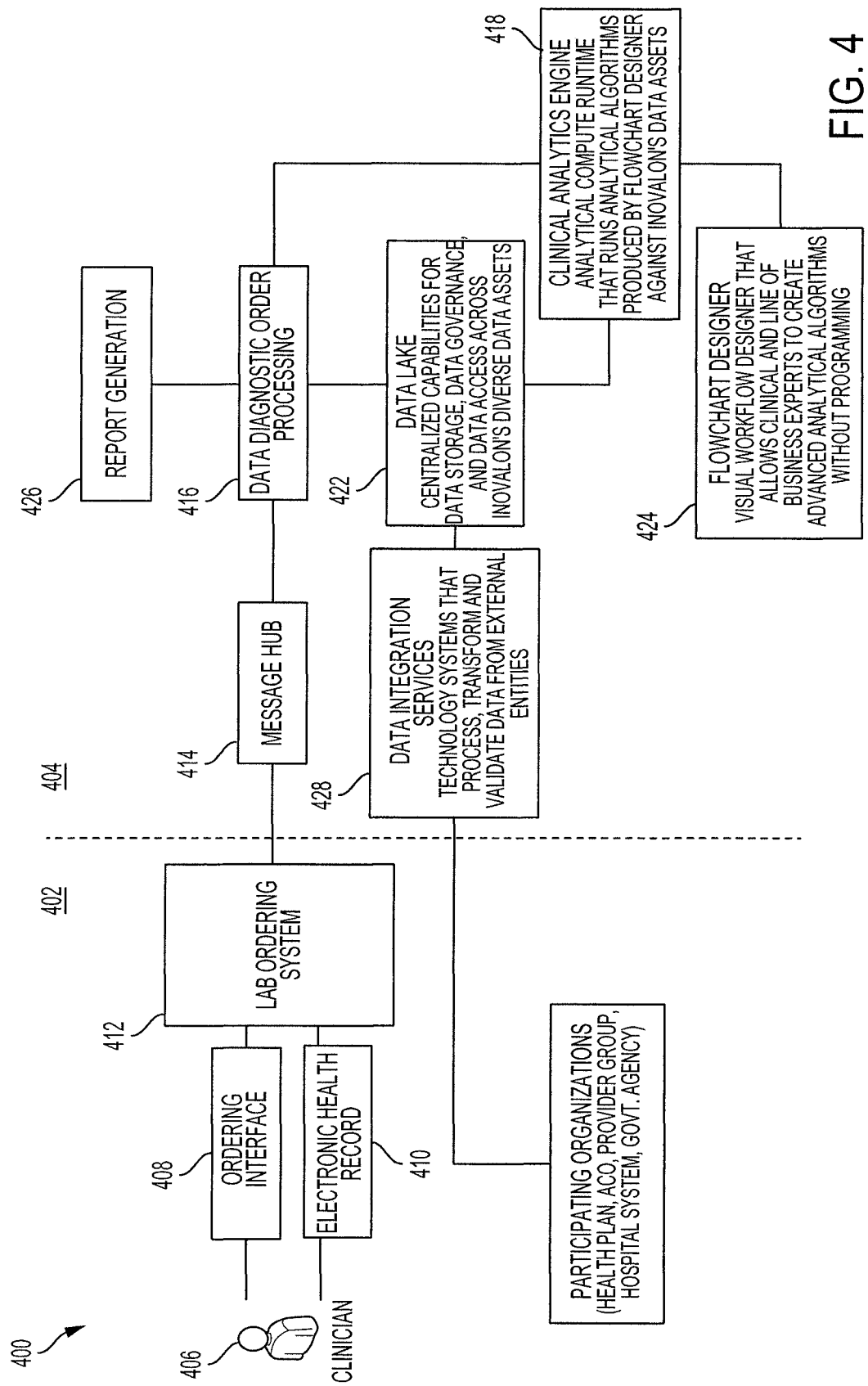
FIG. 4 illustrates an exemplary computing platform for performing an on-demand real-time patient-specific data analysis according to examples of the disclosure.

FIG. 4 illustrates an exemplary computing system to perform on-demand real-time patient-specific data analyses according to examples of the disclosure. The computing system of FIG. 4 can include two primary components, the external interface portion 402, and the on-demand real-time patient-specific data analyses computing platform portion 404. The external interface portion 402 of the computing system 400 can include the components of the computing system that are external to the web service, as previously discussed. For example, the external interface portion 402 of the computing system 400 can include a clinician 406. FIG. 4 can illustrate an exemplary overview of the real-time patient-specific data analysis computing platform according to examples of the disclosure.

As previously discussed, the on-demand real-time patient-specific data analysis requester (i.e., a user) can include a healthcare provider who wishes to order an on-demand real-time patient-specific data analysis for a patient under care. The clinician 406 can utilize numerous types of interfaces to order such a diagnostic. In the example of FIG. 4, two such example interfaces are illustrated. An on-demand real-time patient-specific data analysis requestor can utilize an ordering interface 408, which can be a user interface for a lab-ordering system or prescription drug ordering system as previously described. The ordering interface 408 can be used to order a laboratory service such as blood work, and the same ordering interface 408 can also (as previously discussed) be used to order, route, and distribute on-demand real-time patient-specific data analysis services.

A clinician 406 can also utilize an electronic health record interface or other order entry platform 410 to order an on-demand real-time patient-specific data analysis. An electronic health record (EHR) is an electronic version of a patient's medical history that is maintained by a healthcare provider. In some examples, a healthcare provider is able to look through the patient's medical history using an EHR and, in the same interface, is able to order laboratory work to be performed upon the patient. Using this interface 410, a clinician 406 can request an on-demand real-time patient-specific data analysis in substantially the same way as they would a laboratory diagnostic or prescription drug. Similarly, other order entry platforms may be applied for the ordering of a data diagnostic. Examples include medication order platforms, radiological test order entries, other such order entry systems, or platforms dedicated to the ordering of data diagnostics.

Once a clinician 406 has requested an on-demand real-time patient-specific data analysis using an interface 408 or 410, the order can then be sent to an-ordering system 412. As previously discussed, an-ordering system 412 is an internal processing and communication system by which a provider fulfills orders provided to it from external user interfaces, such as those illustrated at 408 and 410. The-ordering system can process orders using its own internal processes and can route on demand real-time patient-specific data analysis requests to a computing platform 404 to be processed. In this way, an-ordering system can be utilized as a distributor of on-demand real-time patient-specific data analysis services, while the on-demand real-time patient-specific data analysis computing platform 404 can provide the actual on-demand real-time patient-specific data analysis service that is to be delivered to the patient.

Computing platform 404 can include a message hub 414. Message hub 414 can act as the interface between the computing platform 404 and external entities such as the-ordering system 412. Message hub 414 can provide communication capability to the computing platform 404 that can accept orders and provide reports to stakeholders with the results of the on-demand real-time patient-specific data analysis.

Figure 5:
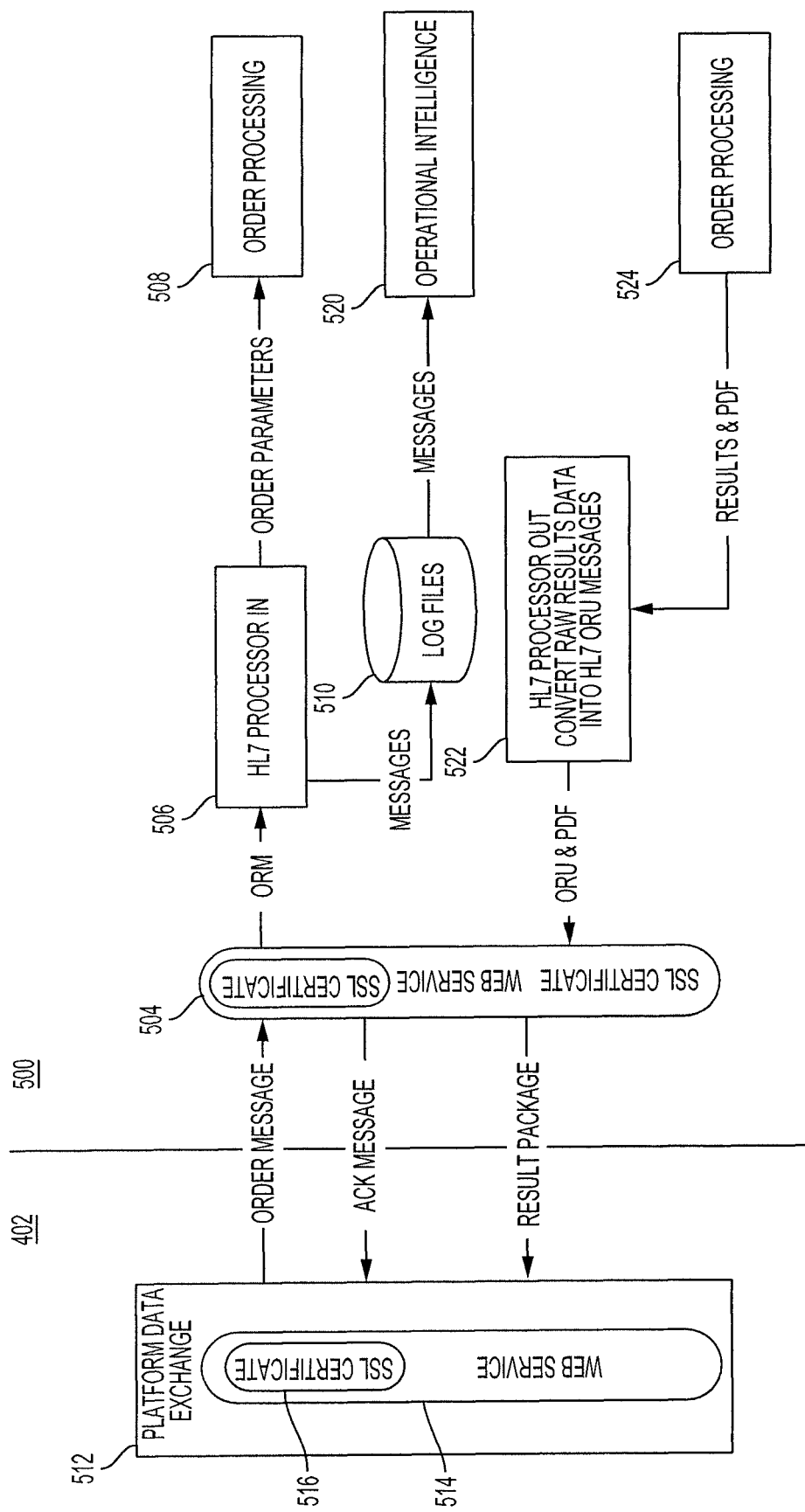
FIG. 5 illustrates an exemplary message hub according to examples of the disclosure.

FIG. 5 illustrates an exemplary message hub according to examples of the disclosure. For purposes of illustration, the interface between the message hub 504 and a laboratory data exchange 402 is also shown. As previously discussed in FIG. 4, the ordering system 412 can act as the interface between a clinician 406 who orders an on-demand real-time patient-specific data analysis, and a computing platform 404. Returning to the example of FIG. 5, the ordering system 412 can include a platform data exchange 512. The platform data exchange 512 can provide a web/network interface between the-ordering system 412 and the computing platform 404.

The platform data exchange 512 can include a web service 514. Web service 514 can initiate and execute communication between the platform data exchange 512 and the on-demand real-time patient-specific data analysis computing platform via the web service 504 located within the message hub. In one example, the web service 514 from the platform data exchange and the web service 504 located in the message hub center can exchange secure socket layer (SSL) certificates 516.

SSL certificates can be passed from the message hub of the on-demand real-time patient-specific data analysis computing platform to the platform data exchange in order to establish the identity of the on-demand real-time patient-specific data analysis platform to the platform data exchange. The SSL certificate 516 can be used to open and establish a secure communications socket between the platform data exchange and the message hub center.

Once an order for an on-demand real-time patient-specific data analysis has been received by the message hub center, it can be sent to input processor 506. Input processor 506 can take the order and convert the order into a format that can be read by the components that will perform the actual processing of the on-demand real-time patient-specific data analysis. In one example, the computing platform can employ a health level seven (HL7) protocol, which is known by one of skill in the art. The input processor 506 can input the order for an on-demand real-time patient-specific data analysis and convert into HL7 format so as to be used by the on-demand real-time patient-specific data analysis computing platform.

Once a received order has been converted into the appropriate format it can be transmitted to an order-processing step 508, described in detail further below. In addition, the order message can be sent to a log file database 510 where the orders received by the system can be archived. The log file database 510 can be accessed by operational intelligence software 520. Operational intelligence software 520 can perform various queries on the log file database 510 to perform various analyses on the orders that are received by the computational platform. The types of analyses can include, for example, an analysis on the types of orders received, an analysis on the organizations or individuals who are ordering on-demand real-time patient-specific data analyses, and other information that could be gleaned from studying the orders received by an on-demand real-time patient-specific data analysis computing platform.

At step 524, an order that has been processed can be sent back to the message hub 500. In some examples the processed order can be sent back in a raw (unedited) format or in some cases, simultaneously, can be sent as a pdf file that has a report of the results. The order can be received by an output processor 522 that can convert the raw-results data in an HL7 observation result message (ORU) or as a pdf file, and in other examples, can simply pass along the pdf that was received from the order processing step 524.

In some examples, the output processor can transmit results in multiple file formats so that the consumer of the on-demand real-time patient-specific data analysis and/or the user interface employed by the user can select the output format that it desires. The output file formats can be transmitted back to the user via the web service 504 of the message, which can relay the results package back to the web service 514 of the platform data exchange 512.

Returning to FIG. 4, once an order has been received and processed by the message hub as discussed above, the order can be transmitted to an on-demand real-time patient-specific data analysis order processing system 416. The role of the on-demand real-time patient-specific data analysis order processing system 416 can be to orchestrate the technologies that may be needed to fulfill the on-demand real-time patient-specific data analysis order.

Figure 6:
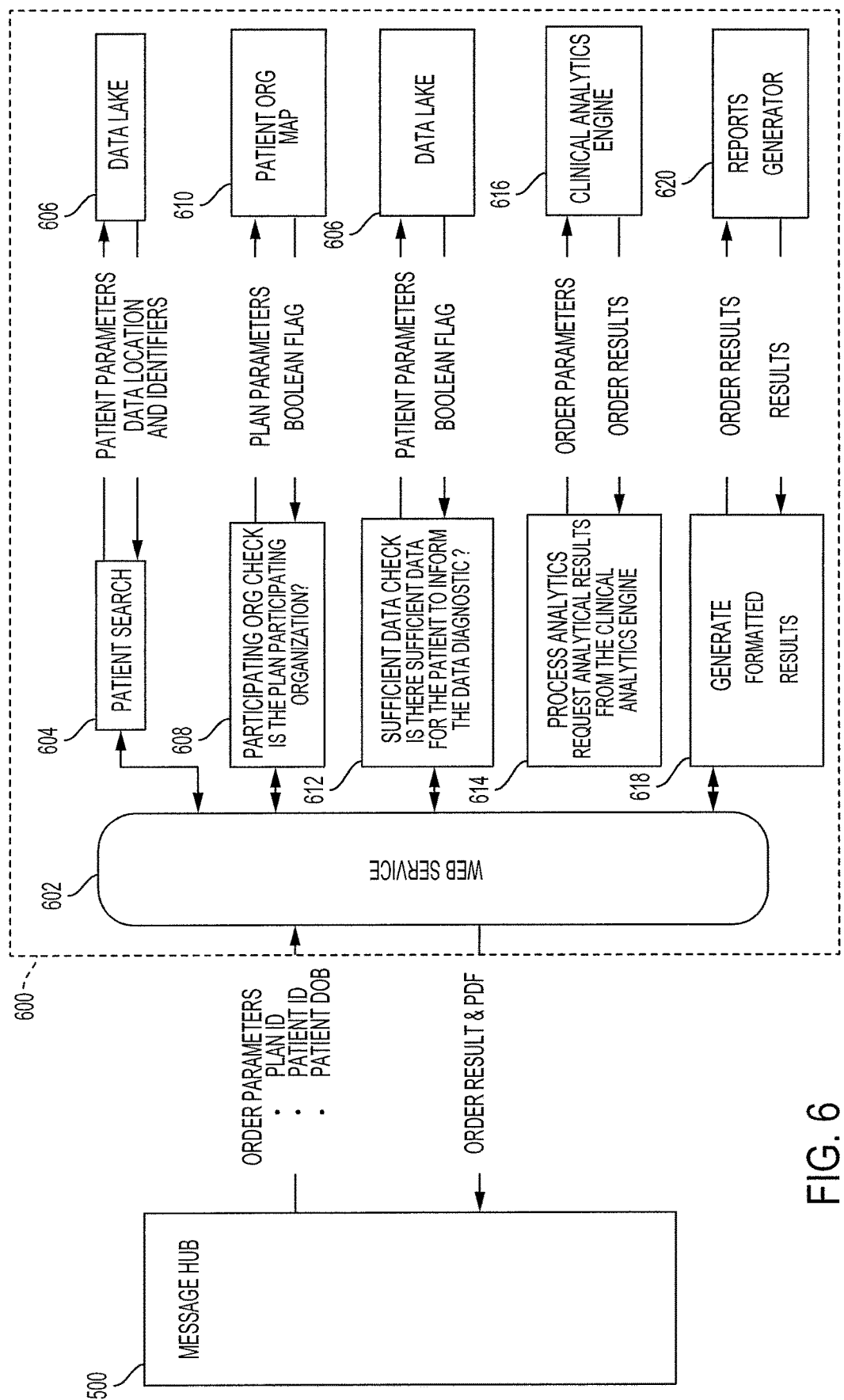
FIG. 6 illustrates an exemplary order-processing architecture according to examples of the disclosure.

FIG. 6 illustrates an exemplary order processing architecture according to examples of the disclosure. As previously discussed, the message hub 500 can transmit order parameters to the order processing component 600. The transmission of the parameters can be facilitated by a web service 602 located within the order processing component 600. The web service 602 can facilitate transmission to and from the order processing component 600 in substantially the same way as the web service described with respect to the message hub of FIG. 5.

At step 604 the order processing component can initiate a patient search as previously described with respect to step 328 of FIG. 3. As part of the patient search, the patient's parameters (i.e., name, date of birth, or other identifying information) can be queried against a data lake 606. Data lake 606 can represent one or more databases that contain information relating to a patient as described above with respect to FIGS. 1-3. At step 604 the data lake 606 can be queried with the patient's parameters, and the data lake can return any data locations and identifiers that relate to the patient.

If the order processing component is able to extract data location and identifiers from the data lake based on the patient's parameters, then it can establish that the patient exists within the system. If, however, the system cannot extract any data locations or identifiers from the data lake 606, then the system can return an error message in accordance with step 322, described with respect to FIG. 3.

As part of the order processing, the system can also check if there is sufficient data to perform an on-demand real-time patient-specific data analysis. At step 612, the order processing component can initiate a search of the data lake 606 using the patient's parameters to determine if there is sufficient data for the patient to inform the on-demand real-time patient-specific data analysis. This process was previously described with respect to step 328 of FIG. 3. If it is determined that insufficient data exists, then the system can return an error message in accordance with step 322, described with respect to FIG. 3. The data lake can return a Boolean flag (set to either 1 or 0) to indicate whether sufficient data exists. The data lake can also return a detailed flag (set to one of many indicators) to indicate the manner of data that was insufficient, in such cases.

At step 608 a participating organization check can be initiated as described with respect to step 326 of FIG. 3. A patient's plan parameters can be transmitted and queried against a participating organization map 610. Participating organization map 610 can be a list of organizations that authorize an on-demand real-time patient-specific data analyses. If the patient's healthcare organization participates in and authorizes on-demand real-time patient-specific data analyses, a Boolean flag may be returned indicating that the diagnostic is authorized. A detailed flag (set to one of many indicators) may also be returned to indicate the manner of authorization or lack of authorization, in such cases. If the diagnostic is not authorized, an error message can be delivered as described in step 322 of FIG. 3.

At step 614, if the checks initiated at steps 604, 608, and 612 all yield positive results, the process can move to a process analytics step in which analytical results from the clinical analytics engine 616 (described in further detail below) can be requested. At step 614, the order parameters can be transmitted to clinical analytics engine 616, which can perform the requested analysis and return the results. A discussion of the clinical analytics engine is provided further below.

At step 618, once the clinical analytics engine 616 produces the results, the results can be sent to a reports generator 620 that can convert the results into a desired format for consumption by a user. The reports generator is discussed further below.

Thus, as discussed above, the order processing component 600 can orchestrate individual components, including the data lake 606, the participating organization map 610, the clinical analytics engine 616, and the reports generator 620, in order to process an on-demand real-time patient-specific data analysis order and return the results back to the user.

Returning to FIG. 4, and as previously discussed the on-demand real-time patient-specific data analysis order processing unit 416 can be connected to a clinical analytics engine 418. The clinical analytics engine 418 can provide the analytical computing runtime environment that runs analytical pre-programmed algorithms or data analytical schemes against data storage assets that are accessible by the computing platform such as the databases stored within data lake 422.

Figure 7:
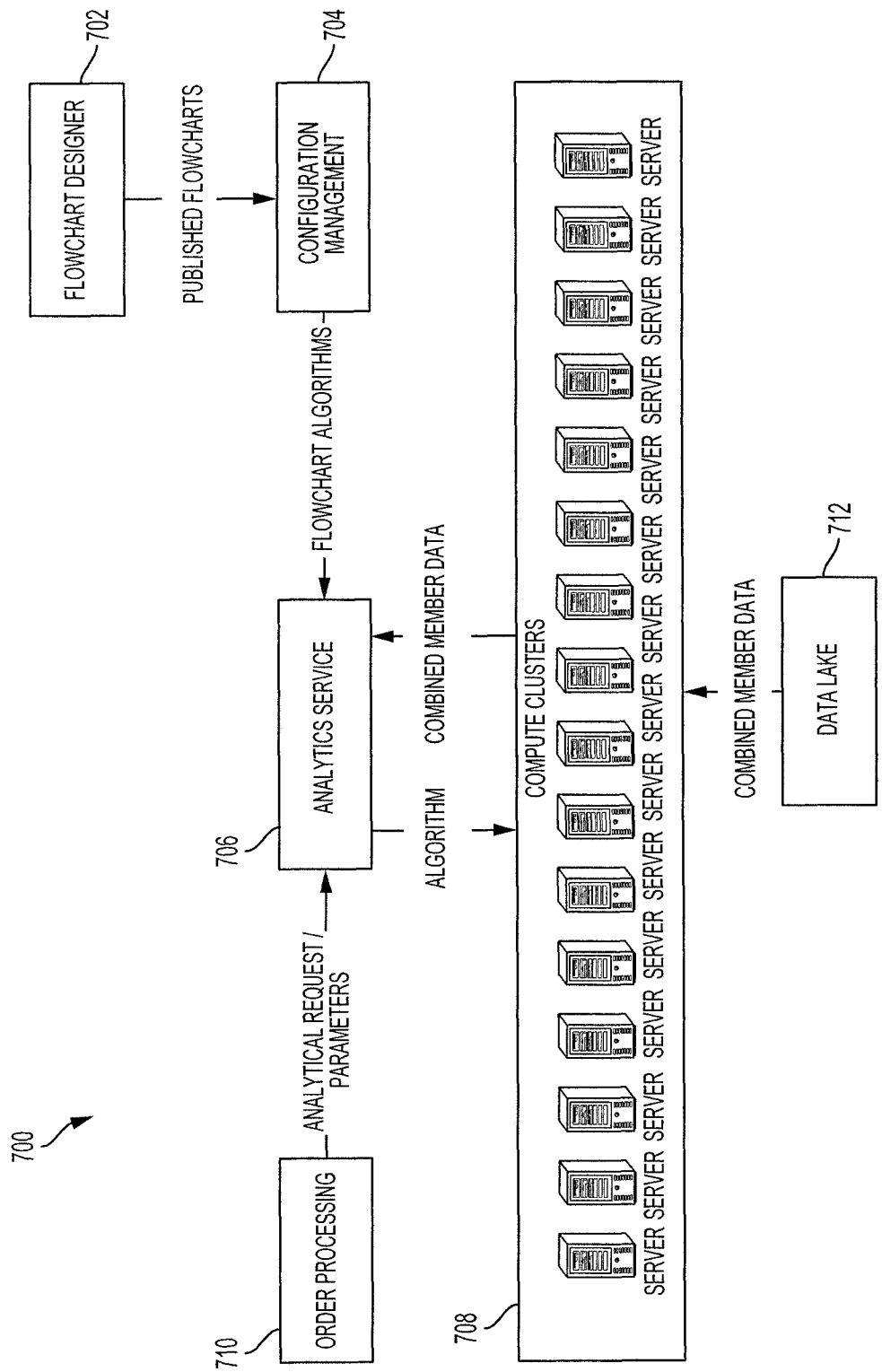
FIG. 7 illustrates an exemplary clinical analytics engine according to examples of the disclosure.

FIG. 7 illustrates an exemplary clinical analytics engine according to examples of the disclosure. The clinical analytics engine can include a configuration management module 704, an analytics service 706, and a computing cluster 708.

The configuration management module 704 can be responsible for establishing and maintaining consistency of the algorithms and data analytical schemes produced by the flowchart designer 702 (described in further detail below).

The analytics service 706 can perform the on-demand real-time patient-specific data analysis by processing the order received from an order processing module 710. The analytics service 706 can perform this task by analyzing the request received from the order processing module 710 and ensuring that the appropriate data from data lake 712 is analyzed using an appropriate algorithm or sets of algorithms in order to ensure that the on-demand real-time patient-specific data analysis is performed per the user's specification.

As previously discussed, an on-demand real-time patient-specific data analysis order can initiate one or more data analytical schemes or algorithms to be performed upon a set of data. The algorithms or data analytical schemes can be created by a flowchart designer 702. Flowchart designer 702 can be a platform by which a programmer can pre-program one or more algorithms and specify how an algorithm is to analyze pertinent data related to a particular on-demand real-time patient-specific data analysis. In one example, flowchart designer 702 can act as a common translator of logical considerations into algorithmic processes applied against the data. As previously discussed, each data analytical scheme or algorithm can include a series of inclusion and exclusion criteria. The exclusion and inclusion criteria can be specified by a user and also can be dictated by the type of on-demand real-time patient-specific data analysis that a user orders.

Using the flowchart designer, a programmer can input the inclusion and exclusion criteria of a search, using a user-friendly syntax, which can then be translated/compiled into an algorithmic process that can be applied against a set of data to perform the on-demand real-time patient-specific data analysis. The analytics service 706, upon receiving an order, can determine which algorithm or set of algorithms is to be applied to a set of data.

The analytics service 706 can also search and extract patient data from the data lake 712. As previously discussed, the order will include identification information relating to the patient for which the on-demand real-time patient-specific data analysis has been ordered. Using such information, as well as inclusion and exclusion criteria provided by the algorithm, the analytics service 706 can extract patient data from data lake 712. Data lake 712 can include internal and external databases, or other data services, as previously discussed above.

The analytics service can extract the desired data from the data lake 712 and then implement the algorithm or algorithms that have been determined to be pertinent to fulfilling the on-demand real-time patient-specific data analysis request. In order to provide the processing power and speed needed to perform a large number of algorithms on a large data set efficiently, the analytics service 706 can utilize a computing cluster 708. The computing cluster 708 can include one or more servers which provide the processing capability required to execute one or more algorithms. In this way, the analytics service 706 can customize the number of servers used to process data based on the processing needs required by the specific data analytic and user information that is under analysis.

Returning to FIG. 4, the clinical analytics engine 418 can receive orders from on-demand real-time patient-specific data analysis order processing module 416. The received order can determine what data is mined and extracted from data 422 and which algorithm designed in flowchart designer 424 is used to analyze the extracted data. The flowchart designer 424 can act as an interface between a programmer who wishes to create data analytical schemes and algorithms that are initiated upon receipt of a specific on-demand real-time patient-specific data analysis order.

Figure 8:
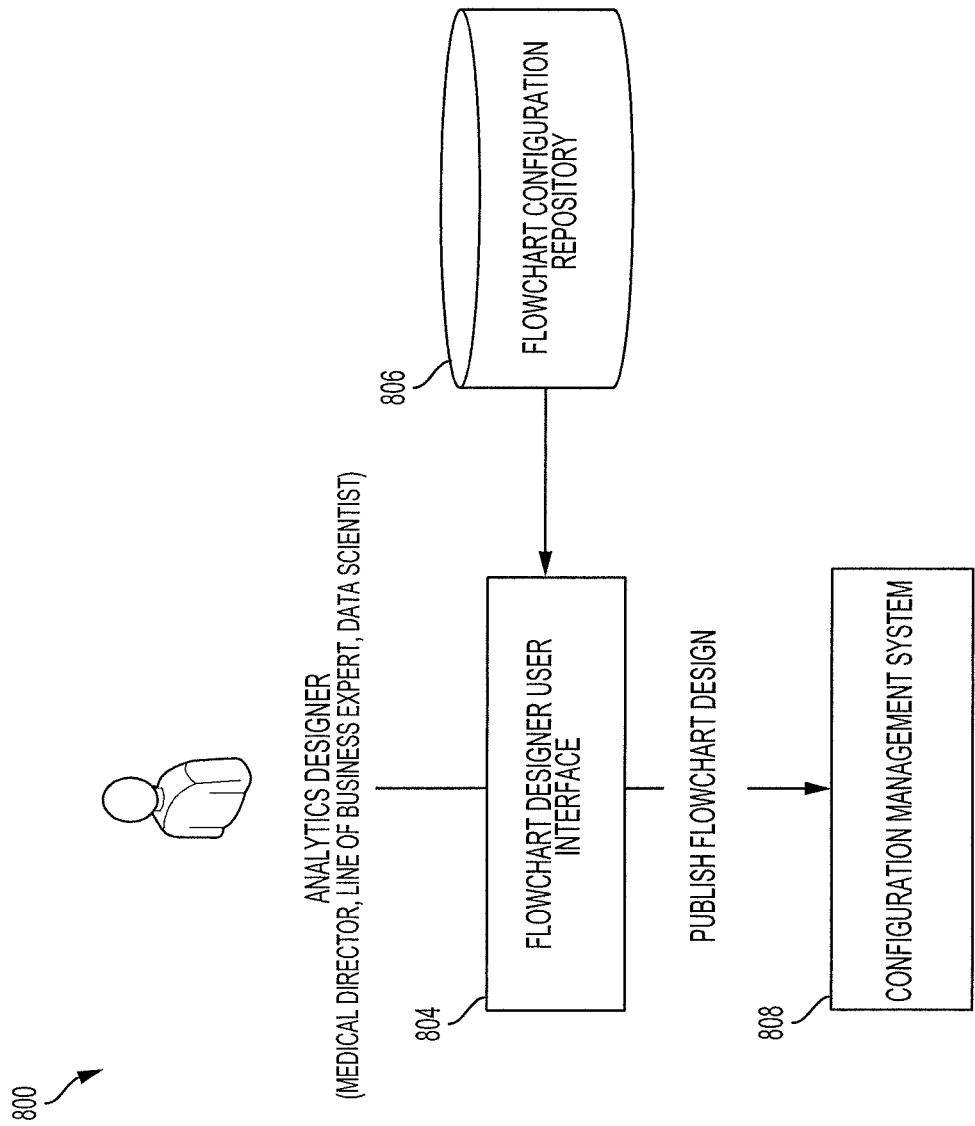
FIG. 8 illustrates an exemplary flowchart design process according to examples of the disclosure.

FIG. 8 illustrates an exemplary flowchart design process according to examples of the disclosure. The design process illustrated in FIG. 8 illustrates how a programmer of the data analytics computing platform can create a pre-programmed algorithm or data analytical scheme that can be executed when a specific on-demand real-time patient-specific data analysis is ordered as outlined above.

A user 802 can access a flowchart designer toolset via a flowchart designer user interface 804. The flowchart designer toolset can provide a set of user-friendly tools for the design, development, and deployment of a broad set of healthcare data analytics algorithms suited to perform various types of on-demand real-time patient-specific data analyses as in the examples provided above. The user interface 804 can be configured such that users of the tool set can achieve superior analytical functionality without having advanced programming experience or training. In other words, the user interface 804 can provide a platform such that a user can provide analytical functionality in a user-friendly syntax which can then be converted into an esoteric description of the algorithm that can be consumed by computing platform for processing.

The user interface 804 can provide a user with access to a flowchart configuration repository 806. Flowchart configuration repository 806 can contain a number of pre-programmed algorithm modules. The user 802 can customize the pre-programmed algorithm modules stored in repository 806 by specifying further inclusion and exclusion criteria as well as specifying exclusion and inclusion criteria that can be specified by the user of the on-demand real-time patient-specific data analysis computing platform.

Once a user/programmer 802 creates an algorithm or data analytical scheme, the process can move to the configuration management system 808 wherein published algorithms can store the various configurations of the algorithm and manage their use and deployment within the on-demand real-time patient-specific data analysis computing platform.

Returning to FIG. 4, once the clinical analytics engine performs the on-demand real-time patient-specific data analysis, it can transmit a result of the on-demand real-time patient-specific data analysis back to on-demand real-time patient-specific data analysis order processing module 416. The on-demand real-time patient-specific data analysis order processing module 416 can take the received result and generate a report that can ultimately be consumed by a user of the on-demand real-time patient-specific data analysis computing platform 404. In one example, the on-demand real-time patient-specific data analysis order processing module 416 can access a report generation module 426 which can format the received results according to defined template that can be pre-defined for a specific type of on-demand real-time patient-specific data analysis.

Figure 9:
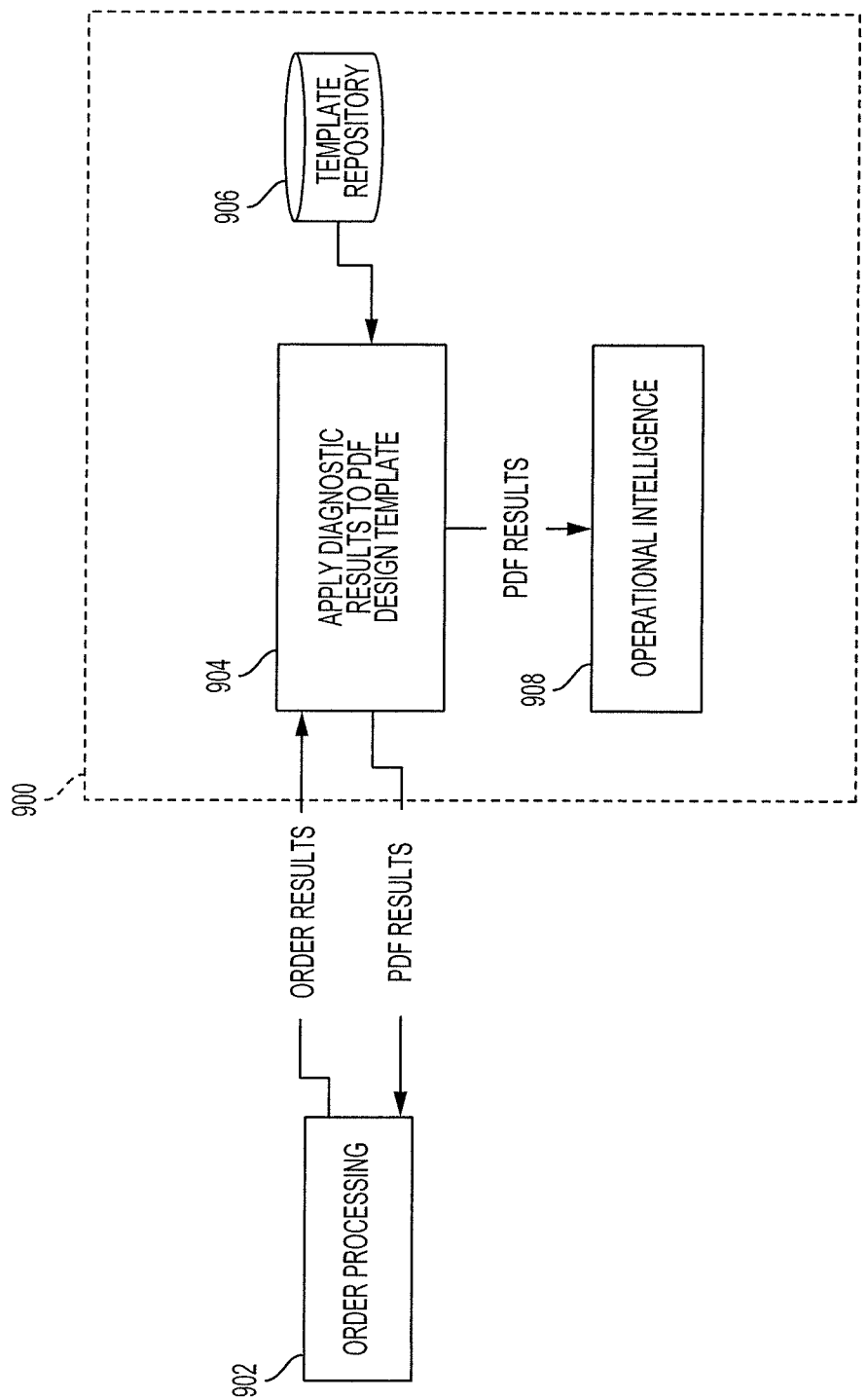
FIG. 9 illustrates an exemplary pdf generator architecture according to examples of the disclosure.

FIG. 9 illustrates an exemplary reports generator architecture according to examples of the disclosure. As previously discussed with respect to FIG. 4, once the results of a processed on-demand real-time patient-specific data analysis are received by an order processing module 902, the order processing module can send the results to a reports generator module 900. The reports generator module 900 can receive the order results and apply the order results to a pdf design template or other output format at module 904. At module 904, the results can be analyzed to determine what type of on-demand real-time patient-specific data analysis pertains to the results. Based on the determined type, the reports generator 900 can access template repository 906 to generate the final report in varying formats.

Template repository 906 can, in one example, store a plurality of report templates, with each report template within the repository pertaining to one or more on-demand real-time patient-specific data analyses that can be executed by the on-demand real-time patient-specific data analysis computing platform. Upon determining the type of on-demand real-time patient-specific data analysis that was performed by the computing platform and reflected within the results, the order processing module 904 can access the template repository, extract the appropriate report template, and generate a report using the received results.

Once the reports generator 900 has generated the report, it can then transmit it back to the order processing module 902 to be ultimately transmitted to a user of the on-demand real-time patient-specific data analysis computing platform. In one example, the reports generator component 900 can also transmit the generated report to an operational intelligence module 908. The operation intelligence module can store all of the various reports that have been generated and can perform analytics upon the reports so as to recognize various trends in the data as discussed above with respect module 520 discussed with respect to FIG. 5.

Returning to FIG. 4, in some examples, the computing platform 404 can also include a data integration services module 428. Data integration services module 428 can be responsible for populating the data that resides in data lake 422 by processing, transforming, and validating data that is received from external entities such as participating healthcare providers.

Figure 10:
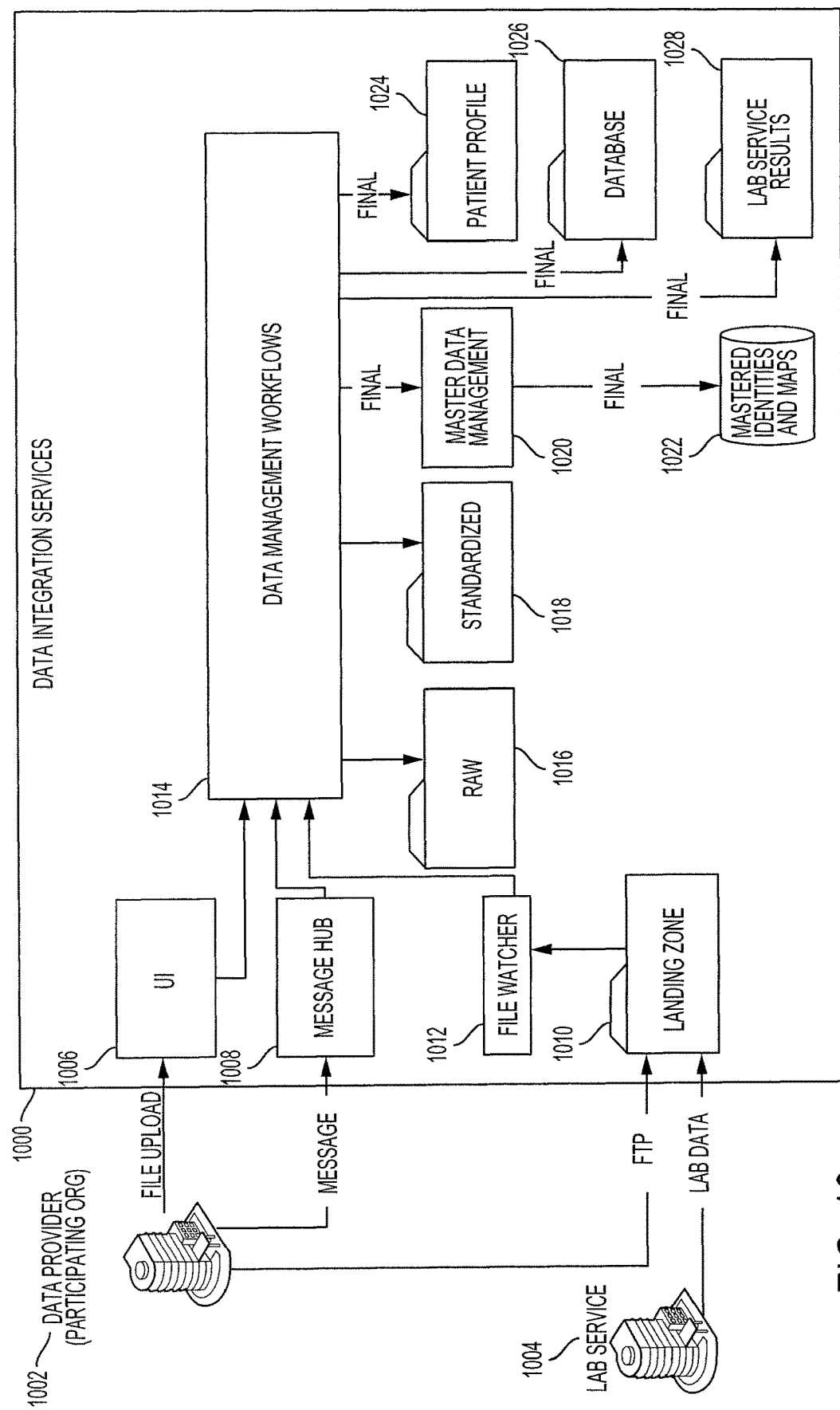
FIG. 10 illustrates an exemplary data integration service according to examples of the disclosure.

FIG. 10 illustrates an exemplary data integration service according to examples of the disclosure. The primary role of the data integration service 1000 can be to ingest data from external entities into the computing platform. Once the data has been ingested, the data integration service 1000 can validate, transform, and organize the data so that the data can be used by the computing platform to execute real-time patient-specific data analyses as described above.

As an example, and not to be interpreted as limiting in any way, participating organization 1002 and Lab service 1004 can serve as examples of external entities that can provide data to the computing platform, and more specifically to the data integration service 1000. Both lab service 1004 and participating organization 1002 can contain data relating to the healthcare of their patients, including but not limited to, information regarding past medical care of a patient as well as other health related information pertaining to their patients.

In one example, and as illustrated in FIG. 10, data integration service 1000 can ingest data from lab service 1004 and participating organization 1002 via three different input paths. The first path to ingest data into the data integration service 1000 can be via a user manually uploading the data to the web-service using a user-interface (UI) 1006. Via the UI 1006 a user can manually upload files to the data integration service 1000 by selecting which file or files they wish to send to the computing platform.

Alternatively, or in addition to the example above, the data integration service 1000 can receive messages using a real-time web-based messaging service that utilizes a message hub 1008 to receive data from the external entities. The message hub 1008 can provide a real-time connection between a data provider such as the participating organization 1002 and the data integration service 1000. Thus, when the participating organization 1002 has new data that it wishes to send to the real-time patient-specific data analysis computing platform, rather than waiting to batch the data with other data to be sent to the computing platform and uploading the data as one batch, the data provider can instead send each data item individually in real-time.

In another example, the data provider and the lab service 1004 can utilize a file transfer protocol (FTP) connection to upload data to the data integration service 1000. A landing zone 1010 can act as file storage that receives data over an ftp connection. A file watcher 1012 can monitor the landing zone 1010 and upload data from the landing zone to the data management workflow 1014 and initiate any workflows necessary to ingest the data (discussed further below) as it is received.

The data management workflows module 1014 can perform various organizational tasks associated with internalizing data received from the external entities such as data provider 1002 and lab service 1004. As an example, data management workflows can include: identity management, wherein the identity of the patients associated with the data to be internalized can be managed, data organization and standardization, wherein data is organized into a standardized format that can facilitate efficient recall of the information, and data quality checks.

The data management workflows 1014 can ultimately organize the data received from the external entities into various data storage entities contained within the data integration service 1000. The raw data, i.e., the data in the form it is received can be stored in a raw data storage 1016. As previously described the received data can be standardized, and, once standardized, the data can be stored in a standardized data storage file system 1018. Standardization can refer to ensuring that that the internalized data is expressed in a form that the computing platform recognizes. As an example of the standardization process, if the computing platform requires that gender is expressed as male, female, and other, but an external entity expresses gender as M, F, and 0, then the standardization process would include translating the M, F, and 0 into male, female, and other.

The data management workflows module 1014 can also initiate a master data management module 1020 that performs one or more algorithms on the data so as to "master" the data. Mastering data can refer to a process in which the various ways in which data belonging to a particular individual can be attributed to that individual. As an example, mastering the data can include recognizing that data attributed to Edward Smith and Ed Smith belong to the same person. Without the mastering process, the system could consider Edward Smith and Ed Smith as two distinct individuals thus leading to the misidentification of data during the performance of a real-time patient-specific data analysis.

As part of the mastering process, the master data management process 1020 can store a series of mastered identities and maps that map the multiple ways to identify an individual to the identity of that particular individual in data storage 1022. The mastered identities and maps storage 1022 can be accessed during a real-time patient-specific data analysis to provide the algorithm a road map for which data to access when performing a real-time patient-specific data analysis on a particular individual.

Once the data is mastered, it can be stored in various file stores and stored in a fashion that optimizes the computing platform's ability to perform data analytics upon the data. As an example, the patient profile data store 1024 can store profiles of each of the patient's that are part of the system. The computing platform can utilize the patient profile data 1024 store to ascertain whether a particular patient exists within the system, and in some examples can also ascertain whether there is sufficient data on a particular patient to perform a real-time patient-specific data analysis.

Database 1026 can represent the primary database in which all of the patient data is stored. The data that populates the database 1026 can be conformed into a format that optimizes the various data analytical analyses performed by the computing platform. For security purposes, the data within database 1026 can be de-identified (as discussed above) and only re-identified once a user of the computing platform has passed through various security and authorization procedures.

Additionally in another example, the data integration service can also maintain a lab service results data store 1028. The lab service results data store can include data received from various lab services providers that is formatted and conformed to a format that the computing platform can operate on to perform real-time patient-specific data analysis analyses.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

What is claimed is:

1. A computer-implemented method comprising:
receiving, by a computing platform, a request to perform a particular analysis of real-time, patient-specific medical data for a particular patient;
before the computing platform obtains real-time, patient-specific medical data that is stored on internal databases for performing the particular analysis and before the computing platform obtains real-time, patient-specific medical data that is stored on multiple external databases for performing the particular analysis, determining, by the computing platform, that an amount of the real-time, patient-specific medical data for the particular patient that is sufficient to perform the particular analysis is likely to be identifiable and available in the multiple external databases;
in response to determining that amount of the real-time, patient-specific medical data for the particular patient that is sufficient to perform the particular analysis is likely to be identifiable and available in the multiple external databases, obtaining, by the computing platform, the real-time, patient-specific medical data that is available in the multiple external databases, using a real-time, transactional data mining technique;
aggregating and transforming, by the computing platform, at least a portion of the obtained data for the particular patient from a stored, accessed, or received format into a different format that the computing platform recognizes and operates on to perform the particular analysis;
performing, by the computing platform, the particular analysis based on the obtained data for the particular patient including at least the portion of the obtained data that was aggregated and transformed;
generating, by the computing platform, a result of performing the requested analysis based on the obtained data for the particular patient including at least the portion of the obtained data that was aggregated and transformed; and
providing, by the computing platform, the result of performing the requested analysis for output.

2. The method of claim 1, wherein the particular analysis comprises a quality of care analysis that assesses a quality of care that the particular patient has received by a provider, and wherein the result of performing the requested analysis comprises an assessment of a quality of care of the particular patient and an indication of remedial steps that are to be undertaken to bring the particular patient within a defined standard of care.

3. The method of claim 1, wherein the requested analysis comprises an analysis that assesses a potential current or future existence of, or a predicted, implication imposed by, a condition, and wherein the result of performing the requested analysis comprises a risk score for the condition.

4. The method of claim 1, wherein the requested analysis comprises an analysis that assesses a potential diagnostic test, inquiry or analysis to be performed to aid in care, quality, risk, waste avoidance, or other improved outcome of the particular patient.

5. The method of claim 1, wherein the requested analysis comprises an analysis that assesses a potential type, venue, duration, timing, or other aspect of a clinical encounter to be undertaken to aid in care, quality, risk, waste avoidance, or other improved outcome of the particular patient.

6. The method of claim 1, wherein the requested analysis comprises an analysis that assesses a potential treatment to be recommended, prescribed, administered, or performed to aid in care, quality, risk, waste avoidance, or other improved outcome of the particular patient.

7. The method of claim 1, wherein the requested analysis comprises a waste-avoidance analysis that assesses potentially unnecessary utilization of tests, and wherein the result of performing the analysis comprises an indication of one or more potentially unnecessary tests or treatments.

8. The method of claim 1, wherein the requested analysis comprises an eligibility analysis that assesses a user's eligibility for various programs, and wherein the result of performing the requested analysis comprises a respective indication of eligibility or applicability for each of the various programs.

9. The method of claim 1, wherein the requested analysis comprises a risk analysis that assesses categories of care, or cost burdens, for a care model or a payment model.

10. The method of claim 1, wherein the request includes inclusion criteria that specifies specific sets of data stored on a data lake that are to be included in the requested analysis.

11. The method of claim 1, wherein the request includes exclusion criteria that specifies specific sets of data stored on a data lake that are to be excluded from the analysis.

12. The method of claim 1, wherein obtaining the patient-specific data:
obtaining one or more data items that are externally stored at an external data source when the request is received.

13. The method of claim 1, wherein the data analysis system is exposed as a web service.

14. The method of claim 1, comprising, after receiving the request, transmitting a secure socket layer (SSL) certificate to an order processing architecture.

15. The method of claim 1, comprising determining, using an organization map, that a user is associated with an organization that authorizes the requested analysis.

16. The method of claim 1, comprises receiving a data including a Boolean flag that indicates that sufficient data exists.

17. A system comprising:
one or more computers and one or more storage devices storing instructions that are operable, when executed by the one or more computers, to cause the one or more computers to perform operations comprising:
receiving, by a computing platform, a request to perform a particular analysis of real-time, patient-specific medical data for a particular patient;
before the computing platform obtains real-time, patient-specific medical data that is stored on internal databases for performing the particular analysis and before the computing platform obtains real-time, patient-specific medical data that is stored on multiple external databases for performing the particular analysis, determining, by the computing platform, that an amount of the real-time, patient-specific medical data for the particular patient that is sufficient to perform the particular analysis is likely to be identifiable and available in the multiple external databases;
in response to determining that amount of the real-time, patient-specific medical data for the particular patient that is sufficient to perform the particular analysis is likely to be identifiable and available in the multiple external databases, obtaining, by the computing platform, the real-time, patient-specific medical data that is available in the multiple external databases, using a real-time, transactional data mining technique;
aggregating and transforming, by the computing platform, at least a portion of the obtained data for the particular patient from a stored, accessed, or received format into a different format that the computing platform recognizes and operates on to perform the particular analysis;

performing, by the computing platform, the particular analysis based on the obtained data for the particular patient including at least the portion of the obtained data that was aggregated and transformed;

generating, by the computing platform, a result of performing the requested analysis based on the obtained data for the particular patient including at least the portion of the obtained data that was aggregated and transformed; and providing, by the computing platform, the result of performing the requested analysis for output.

18. A non-transitory computer-readable medium storing software comprising instructions executable by one or more computers which, upon such execution, cause the one or more computers to perform operations comprising:

receiving, by a computing platform, a request to perform a particular analysis of real-time, patient-specific medical data for a particular patient;

before the computing platform obtains real-time, patient-specific medical data that is stored on internal databases for performing the particular analysis and before the computing platform obtains real-time, patient-specific medical data that is stored on multiple external databases for performing the particular analysis, determining, by the computing platform, that an amount of the real-time, patient-specific medical data for the particular patient that is sufficient to perform the particular analysis is likely to be identifiable and available in the multiple external databases;

in response to determining that amount of the real-time, patient-specific medical data for the particular patient that is sufficient to perform the particular analysis is likely to be identifiable and available in the multiple external databases, obtaining, by the computing platform, the real-time, patient-specific medical data that is available in the multiple external databases, using a real-time, transactional data mining technique;

aggregating and transforming, by the computing platform, at least a portion of the obtained data for the particular patient from a stored, accessed, or received format into a different format that the computing platform recognizes and operates on to perform the particular analysis;

performing, by the computing platform, the particular analysis based on the obtained data for the particular patient including at least the portion of the obtained data that was aggregated and transformed;

generating, by the computing platform, a result of performing the requested analysis based on the obtained data for the particular patient including at least the portion of the obtained data that was aggregated and transformed; and providing, by the computing platform, the result of performing the requested analysis for output.

19. The medium of claim 18, wherein the particular analysis comprises a quality of care analysis that assesses a quality of care that the particular patient has received by a provider, and wherein the result of performing the requested analysis comprises an assessment of a quality of care of the particular patient and an indication of remedial steps that are to be undertaken to bring the particular patient within a defined standard of care.

* * * * *